(12) United States Patent
Alberico et al.

(10) Patent No.: US 8,658,792 B2
(45) Date of Patent: Feb. 25, 2014

(54) CARBANUCLEOSIDE SYNTHESIS AND NOVEL INTERMEDIATE COMPOUNDS USEFUL THEREIN

(75) Inventors: Dino Alberico, Mississauga (CA); Boris Gorin, Oakville (CA); Ryan Beharrilall, Scarborough (CA); Craig Dixon, Brooklin (CA); Joshua Clayton, Oakville (CA); Varghese Rexon, Brampton (CA)

(73) Assignee: Alphora Research Inc., Mississauga, Ontario ( * ) Notice: Subject to any disclaimer, the term of this patent is extended or adjusted under 35 U.S.C. 154(b) by 0 days.

(21) Appl. No.: 13/698,886

(22) PCT Filed: May 30, 2011

(86) PCT No.: PCT/CA2011/050324
§ 371 (c)(1),
(2), (4) Date: Nov. 19, 2012

(87) PCT Pub. No.: WO2011/150513
PCT Pub. Date: Dec. 8, 2011

(65) Prior Publication Data
US 2013/0066071 A1    Mar. 14, 2013

(30) Foreign Application Priority Data

May 31, 2010    (CA) .................................. 2705953

(51) Int. Cl.
*C07D 473/00*    (2006.01)
(52) U.S. Cl.
USPC .......................................................... 544/276
(58) Field of Classification Search
USPC .......................................................... 544/265
See application file for complete search history.

(56) References Cited

U.S. PATENT DOCUMENTS

2011/0201809 A1*   8/2011   Hu et al. ........................ 544/276
2011/0251387 A1*   10/2011   Lee et al. ....................... 544/276

* cited by examiner

*Primary Examiner* — Noble Jarrell
*Assistant Examiner* — Laura Daniel
(74) *Attorney, Agent, or Firm* — McMillan LLP

(57) ABSTRACT

Anti-virally active carbanucleosides such as entecavir are prepared by a process which utilizes, throughout the synthesis, an aromatic protectant group for the hydroxyl and the alkyl hydroxy groups of the starting material, removed as the final step of a multi-step synthesis. Such protectant groups yield intermediates which are solid and therefore easily purified at various stages of the process, for an economical and relatively fast process for synthesizing the final product.

9 Claims, 1 Drawing Sheet

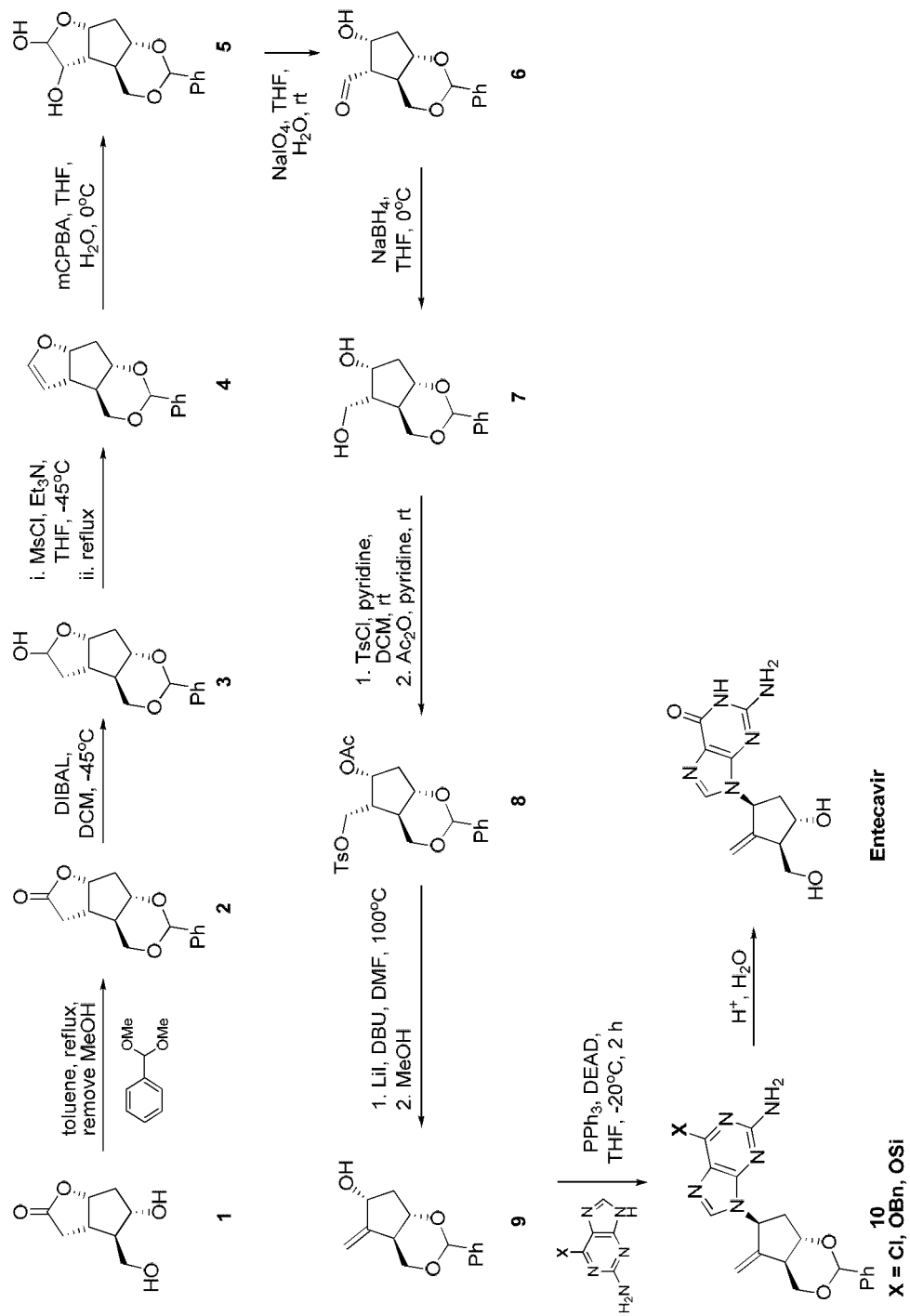

CARBANUCLEOSIDE SYNTHESIS AND NOVEL INTERMEDIATE COMPOUNDS USEFUL THEREIN

FIELD OF THE INVENTION

This invention relates to processes and intermediates for use in preparing anti-viral compounds. More particularly, it relates to chemical synthesis of anti-viral carbanucleoside compounds having a cyclopentanol ring bonded to a nitrogen heterocycle such as a purine or pyrimidinone, as exemplified by entacavir (2-amino-1,9-dihydro-9-((1S,3R,4S)-4-hydroxy-3-(hydroxymethyl)-2-methylenecyclopentyl)-28 6H-purin-6-one), and intermediates useful in such synthesis.

BACKGROUND OF THE INVENTION AND PRIOR ART

Entecavir, the structural formula of which is

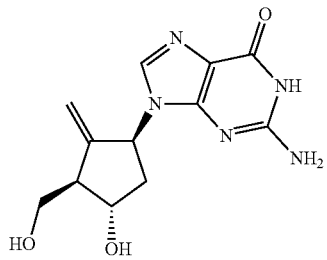

(Ia)

is an anti-virally active pharmaceutical compound used in the treatment of hepatitis B infections in humans. It is marketed under the trade name "Baraclude", as oral tablets and solutions.

Prior art methods of making entecavir involve protection of hydroxyl and hydroxymethyl groups on a cyclopentane starting material with silyl protectant groups, while chemical reaction and derivatization of other groups to form the entecavir molecule are conducted. The silyl protectant groups are removed by hydrolysis in a final or close to final synthetic process step.

There are two significant problems with these prior methods. The first is that the silyl protected intermediates are, in most if not all cases, oils in nature. This renders them difficult to purify. They need the application of chromatographic techniques of purification, which are time-consuming and hence expensive on the commercial scale. The second problem is that the silylated intermediates contain no chromophores capable of absorption of UV light to render them visible in high performance liquid chromatography (HPLC) instrumentation to allow them to be used to track the reactions and determine the purity of the intermediates as they are formed. U.S. Pat. No. 5,206,244 discloses entecavir and analogues thereof, along with methods for their preparation.

It is an object of the present invention to provide a novel synthesis of entecavir and similar compounds, in which these problems are significantly reduced.

SUMMARY OF THE INVENTION

The present invention provides a synthesis of entecavir and similar carbanucleoside compounds, which avoids the use of silyl protectant groups. Instead, the hydroxyl group and hydroxymethyl group on adjacent carbon atoms of the cyclopentane ring are protected with an alkyl aromatic group. The aromatic group (phenyl, naphthyl and the like) is chromophoric, allowing the progress of reactions and the purity of intermediates to be checked on HPLC instrumentation, and adjusted and optimized as necessary. Moreover, the intermediate compounds carrying the aromatic protectant are almost all solid and crystalline, allowing purification of them by simple crystallization.

Thus according to the present invention, from one aspect, there is provided a process of preparing antiviral carbanucleoside compounds of the general formula:

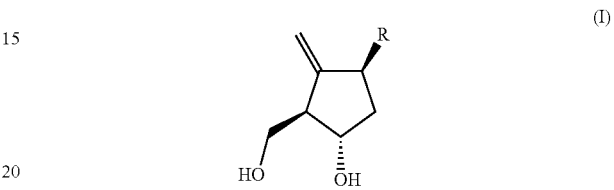

(I)

where R represents a nitrogen heterocycle selected from purine, adenine, guanine, uracil, thymidine, cytosine and substituted derivatives thereof, which includes the steps of reacting a protected cyclopentanol of formula:

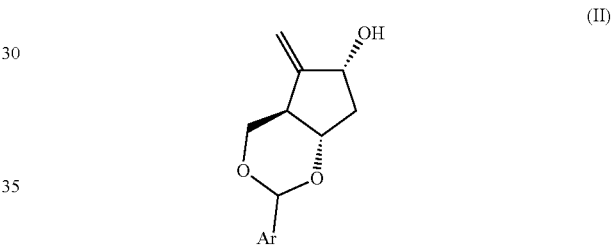

(II)

where Ar is an aromatic nucleus, with an appropriately protected purine, adenine, guanine, uracil, thymidine, cytosine or substituted derivative thereof, and subsequently deprotecting the resultant carbanucleoside to produce a compound of formula I.

From another aspect, there is provided intermediate compounds useful in the synthesis of carbanucleosides of formula (I) given above, and having the structural formula (II) given above, in which Ar represents an aromatic nucleus.

From another aspect, there is provided intermediate compounds useful in the synthesis of carbonuclesides of formula (I) given above, and having the structural formula (IV), in which Ar represents aromatic nucleus.

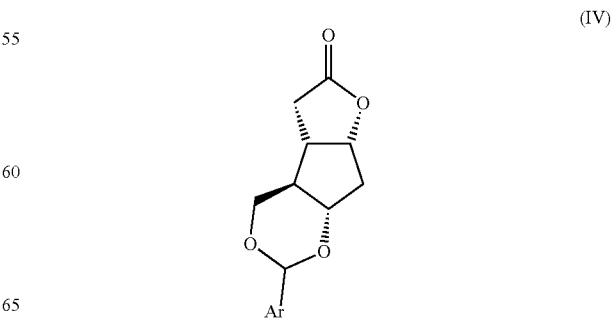

(IV)

BRIEF REFERENCE TO THE DRAWING

The attached single FIGURE of drawings depicts the preferred overall synthetic scheme for preparing entecavir according to the invention.

THE PREFERRED EMBODIMENTS

The preferred choice for group Ar is phenyl, on account of the fact that such intermediate can be prepared from the readily available starting materials, Corey lactone diol of formula I on the accompanying FIGURE of the drawings and benzaldehyde dimethyl acetal. Analogous materials having other aromatic groups such as inertly substituted phenyl naphthyl and the like can be synthesized and used, if desired, provided that any such substituents do not interfere with the subsequent reactions.

Thus the first reaction step in the preferred process according to the invention is the reaction of Corey lactone diol with benzaldehyde dimethyl acetal to form the ring protected diol 2 shown on the accompanying drawing. This is suitably accomplished in an inert aromatic solvent such as toluene, under reflux, with removal of the methanol so formed. The product 2 is a solid which can be filtered off and purified by simple washing.

Next, the protected diol 2 is reduced to a lactol 3. This can be done with an organometallic reducing agent such as dibutylaluminum hydride, DIBAL, in solution at low temperatures, suitably below −20° C. Again the product 3 is a solid, obtainable by evaporation of the product solution to dryness. Purification of lactol 3 prior to the next reaction step is unnecessary.

For the reaction step to form compound 4, a vinyl ether, reaction of compound 3 with methanesulfonyl chloride in the presence of triethylamine, at similar low temperatures is preferred. Tetrahydrofuran is a suitable solvent, and the methanesulfonyl chloride is best added dropwise to the reaction mixture. The resultant vinyl ether is a solid, which can be recovered by filtration and washed for purification purposes.

The vinyl ether 4 is then converted to a diol 5, by oxidation in solution with, e.g., 3-chloroperbenzoic acid or the like, at temperatures around 0° C. Again, THF is a suitable solvent. The cyclopentane diol so formed is a solid material, recoverable by filtration, and can be purified to a satisfactory degree by simple washing, ready to proceed to the next step.

Next, the diol 5 is converted to aldehyde, compound 6 on FIG. 1, by ring opening oxidation using a strong oxidizing agent such as sodium periodate. A mixture of THF and water is suitable as a solvent, with the product 6, which again is a solid, dissolving in the organic layer. It can be recovered from the separated organic layer by concentration and filtration. Further purification prior to the next reaction step is unnecessary.

The next reaction step is the reduction of the aldehyde 6 to form the cyclopentane diol 7. A suitable reducing agent for this purpose is sodium borohydride, again in THF solvent. Once again, the product is solid, recoverable by filtration, to be washed and dried before the next step of the procedure.

Prior to reaction to introduce the methylene group at position 2 of the cyclopentyl nucleus, the hydroxyl groups of compound 7 should be protected. Tosyl is the preferred protectant group for the hydroxymethyl group, so that the next step in the preferred reaction sequence is reaction of compound 7 with p-toluenesulfonic acid or a halide thereof in pyridine-dichloromethane solvent. When this reaction has been completed, acetic anhydride in pyridine can be added to the reaction mixture, and the tosyl acetate compound 8 formed. After concentration of the organics, the compound 8 can be recovered by filtration as a solid.

Next, the tosyl acetate compound 8 is converted to the allyl alcohol 9. This is suitably accomplished by reaction with lithium halide and 1,8-diazabicyclo[5.4.0]undec-7-ene DBU in dimethylformamide solvent, at elevated temperature, followed by addition of methanol to hydrolyze the acetate group to hydroxyl. The product 9 can be recovered by solvent extraction, and concentrated to yield a solid.

The next step is the coupling of the compound 9 with a selected nucleoside, appropriately protected to ensure coupling through a nuclear nitrogen group to the hydroxyl function of the cyclopentyl nucleus. In the case of preparation of the preferred carbanucleoside of the invention, entecavir, the nucleoside is a protected guanine. Suitable protectant groups include Cl, OBn and OSi. This reaction of compound 9 to produce the entecavir precursor 10, can be accomplished with triphenyl phosphine and diethyl azodicarboxylate DEAD, in THF solvent at temperatures below 0° C. It simply remains to remove the protectant group from the nucleoside portion of the molecule, e.g. by acid hydrolysis to complete the preparation of the final carbanucleoside compound.

The invention will be further described, for illustrative purposes, with reference to the following experimental examples of the most preferred embodiment of the process of the invention.

Specific Description of the Most Preferred Embodiment

This section is to be read with reference to the accompanying FIGURE of drawings, illustrating the route of chemical synthesis according to the most preferred embodiment.

Example 1

Preparation of Corey Lactone Benzylidene Acetal (2)

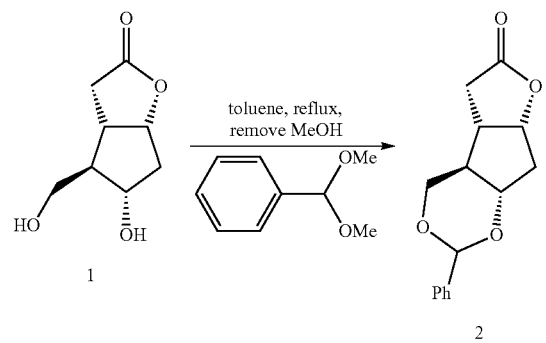

To a suspension of Corey lactone diol (1) (50 g, 290 mmol, 1 equiv) in toluene (1 L) was added benzaldehyde dimethyl acetal (66 g, 435 mmol, 1.5 equiv) and hydrogen chloride solution (4.0 M in dioxane) (1.45 mL, 5.8 mmol, 0.02 equiv). The mixture was heated in an oil bath at 130° C. for 2 h using a Dean-Stark apparatus to remove methanol. Approximately 100-150 mL of methanol/toluene mixture was collected at an internal temperature of 95-108° C. The reaction was cooled in an ice bath and methyl tert-butyl ether (900 mL) was added.

The mixture was stirred for 1.5 h in the ice bath, filtered, and washed with methyl tert-butyl ether (500 mL) to afford 80-85% of 2 as a white solid.

Example 2

Preparation of Vinyl Ether (4)

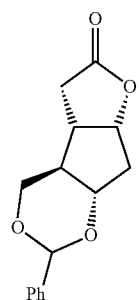

2

DIBAL,
DCM, -45° C.

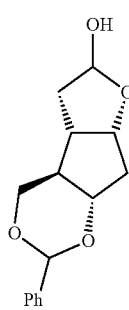

3 i. MsCl, Et$_3$N
THF, -45° C.
ii. reflux

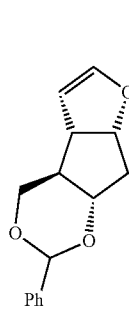

4

To a -45° C. solution of 2 (80 g, 307 mmol, 1 equiv) in dichloromethane (1600 mL) was added diisobutylaluminum hydride (1M in toluene, 338 mL, 338 mmol, 1.1 equiv) dropwise over 1.5 h, followed by stirring for 1 h. The solution temperature was adjusted to -15° C. and pH 7 buffer solution (80 mL) was added dropwise over 45 min. The mixture was warmed to room temperature overnight. The suspension was filtered and the filter cake was re-suspended in dichloromethane (400 mL) and stirred at room temperature for 2 h. The suspension was filtered and the combined filtrates were concentrated to dryness to afford 3 which was used in the next reaction without further purification.

The crude material 3 was dissolved in tetrahydrofuran (1600 mL) and cooled to -45° C. Triethylamine (428 mL, 307 mmol, 10 equiv) was added slowly followed by the dropwise addition of methanesulfonyl chloride (36 mL, 46 mmol, 1.5 equiv). The solution was stirred for an additional 1 h and then heated at reflux for 5 h. The solution was cooled to room temperature and water (800 mL) was added. The tetrahydrofuran was distilled off by heating at 50° C. under vacuum (approximately 800 mL of solvent containing mainly tetrahydrofuan was collected). Water (800 mL) was added and the solution was distilled by heating at 50° C. under vacuum (approximately 800 mL of solvent was collected). To the resulting suspension was added water (800 mL) and the suspension was filtered, washed with water (400 mL) and dried under vacuum to afford 70 g of 4 as a beige solid (93%).

Example 3

Preparation of Cyclopentadiol (7)

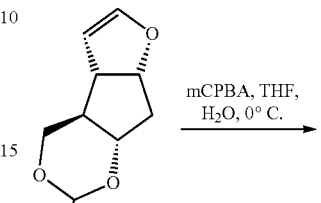

4 mCPBA, THF,
H$_2$O, 0° C.

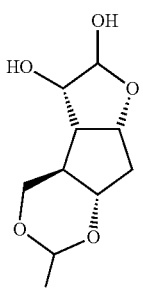

5

NaIO$_4$, THF,
H$_2$O, rt

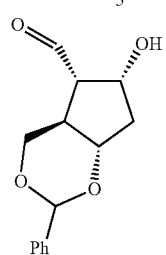

6

NaBH$_4$,
THF, 0° C.

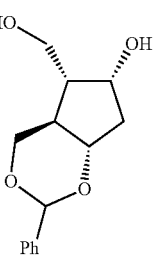

7

To a 5° C. solution of 4 (21.8 g, 89 mmol, 1 equiv) in THF:water (2:1, 330 mL) was added dropwise over 40 min a solution of 3-chloroperbenzoic acid (77%) (22 g, 90 mmol, 1.1 equiv). The resulting mixture was stirred at 5° C. for 45 min and then quenched with 3 N aqueous NaOH to pH 7. The mixture was concentrated under reduced pressure to a thick slurry. The solids were filtered, washed with water, and dried under vacuum to afford 5 as a white solid which was used in the reaction without further purification.

The crude material 5 was dissolved in tetrahydrofuran (615 mL). Water (124 mL) and sodium bicarbonate (225 g, 2.68 mol, 30 equiv) were added and the mixture was cooled to 5° C. Sodium periodate (95 g, 446 mmol, 5 equiv) was added in portions and the resulting suspension was stirred at 5° C. for 1 h. The resulting suspension was filtered and washed with isopropyl acetate (600 mL). To the filtrate was added saturated aqueous sodium bicarbonate (250 mL). The aqueous layer was separated and washed with isopropyl acetate (200 mL). The combined organics were dried over sodium sulfate, filtered, and concentrated to afford 6 as a yellow solid which was used in the reaction without further purification.

The crude material 6 was dissolved in tetrahydrofuran (615 mL) and methanol (61 mL) and the solution was cooled to 5° C. Sodium borohydride (13.5 g, 356 mmol, 4 equiv) was added slowly and mixture was warmed to room temperature overnight. The reaction was quenched with water (300 mL) and extracted with isopropyl acetate (3×200 mL). The organics were concentrated to dryness and the resulting white solid was triturated in methyl tert-butyl ether (50 mL) for 30 min. The solids were filtered, washed with methyl tert-butyl ether and dried under vacuum to afford 10 g of 7 as a white solid (45% over 3 steps).

Example 4

Preparation of Tosyl Acetate (8)

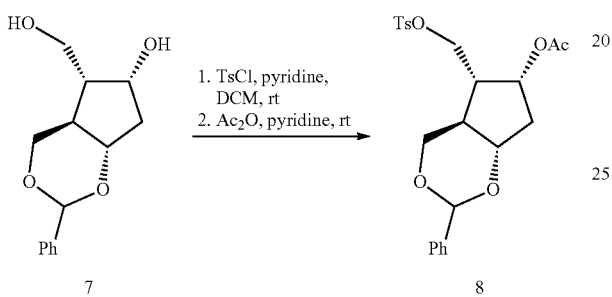

To a solution of 7 (10 g, 40 mmol, 1 equiv) and pyridine (22.6 mL, 280 mmol, 7 equiv) in dichloromethane (200 mL) was added p-toluenesulfonyl chloride (11.4 g, 60 mmol, 1.5 equiv). The mixture stirred at room temperature overnight. Pyridine (22.6 mL, 280 mmol, 7 equiv) and acetic anhydride (21.9 mL, 232 mmol, 5.8 equiv) were added at room temperature and the mixture was stirred overnight. The reaction was cooled to 5° C. and quenched with 2 N aq NaOH to pH 7. The aqueous layer was separated and extracted with dichloromethane (2×50 mL). The combined organics were dried over sodium sulfate, filtered, and concentrated. The resulting semi-solid was dissolved in isopropyl acetate (100 mL) and concentrated to dryness. This was repeated 2 more times. The resulting semi-solid was triturated in methyl tert-butyl ether (250 mL), filtered and dried under vacuum to afford 8.1 g of 8 (45%) as a pale yellow solid.

Example 5

Preparation of Allyl Alcohol (9)

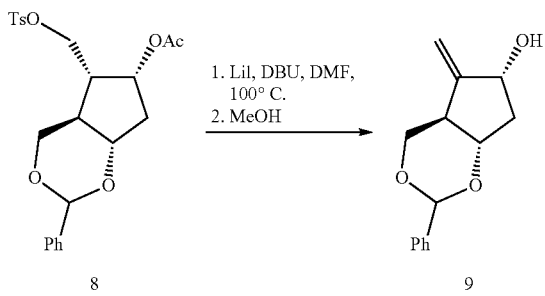

To a solution of 8 (2.5 g, 5.6 mmol, 1 equiv) in DMF (25 mL) was added lithium bromide (1.5 g, 11.2 mmol, 2 equiv) and 1,8-diazabicyclo[5.4.0]undec-7-ene (8.51 g, 56 mmol, 10 equiv). The mixture was heated to 100° C. for 1 h and then cooled to room temperature. Methanol (12 mL) was added and the mixture was stirred at room temperature overnight. Brine (120 mL) and isopropyl acetate (120 mL) were added and the aqueous layer was separated and extracted with isopropyl acetate (2×120 mL). The combined organics were dried over sodium sulfate, filtered, and concentrated. The crude oil was purified by column chromatography using 30% ethyl acetate/hexanes as eluant to afford 0.38 g of 8 as an off-white solid (29%).

Example 6

Preparation of Protected Entecavir Precursor (10)

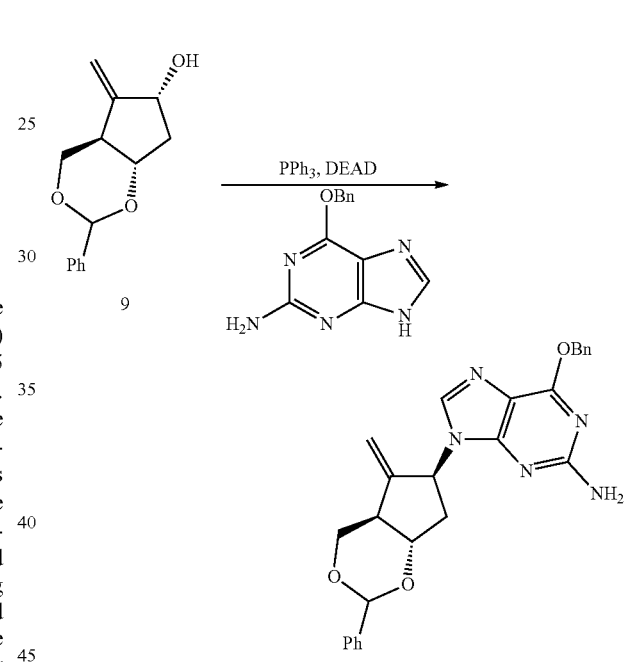

To a 0° C. solution of 9 (180 mg, 0.775 mmol, 1 equiv) and 2-amino-6-benzyloxypurine (260 mg, 0.85 mmol, 1.4 equiv) in tetrahydrofuran was added dropwise a solution of triphenylphosphine (470 mg, 1.78 mmol, 2.3 equiv) and diethyl azodicarboxylate (310 mg, 1.78 mmol, 2.3 equiv) in tetrahydrofuran (10 mL). The mixture was warmed to room temperature overnight. The reaction was quenched with brine (50 mL) and diluted with isopropyl acetate (50 mL). The aqueous layer was separated and extracted with isopropyl acetate (3×50 mL). The combined organics were dried over sodium sulfate, filtered, and concentrated. The crude oil was purified by column chromatography using 50% ethyl acetate/hexanes as eluant to afford 85 mg of 10 as a white solid (24%).

Example 7

Preparation of Entecavir

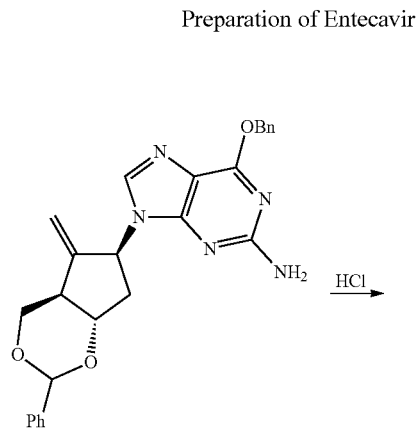

To a solution of 9 (98.7 mg, 0.22 mmol, 1 equiv) in 1,4-dioxane (2 mL) was added HCl (4 M in 1,4-dioxane, 2 mL). The solution was stirred at room temperature overnight and then concentrated to dryness. HCl (2 M in diethyl ether, 2 mL) was added the mixture was stirred at room temperature for 30 min. The resulting precipitate was filtered and washed with diethyl ether (4 mL) to afford 30 mg of entecavir as a light brown solid (43%).

What is claimed is:

1. A process of preparing antiviral carbanucleoside compounds of the general formula:

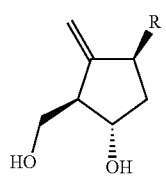

(I)

where R represents a nitrogen heterocycle selected from purine, adenine, guanine, uracil, thymidine, cytosine and substituted derivatives thereof, which includes the steps of reacting a protected cyclopentanol of formula:

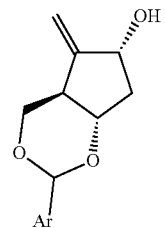

(II)

where Ar is an aromatic nucleus, with an appropriately protected purine, adenine, guanine, uracil, thymidine, cytosine or substituted derivative thereof, and subsequently deprotecting the resultant carbanucleoside to produce a compound of formula I in which the preparation of the protected cyclopentanol of formula (II) involves a step of reacting a Corey lactone diol of formula

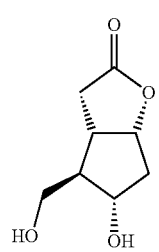

(III)

by reaction with arylaldehyde dimethyl acetal to form the dioxalane protectant ring, and form a compound of formula:

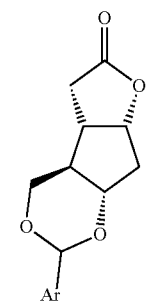

(IV)

in which the compound of formula (IV) is converted to a cyclopentanol aldehyde of formula:

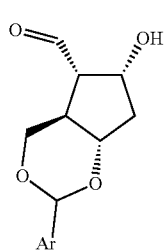

(V)

which is subsequently subjected to reduction to convert the aldehyde function to a hydroxymethyl group, the hydroxyl functions are protected, and then the protected hydroxymethyl group is converted to methylene to produce the compound of formula (II).

2. The process of claim 1, wherein Ar represents phenyl.

3. The process of claim 2 wherein the conversion of the compound of formula (IV) to the cyclopentanol aldehyde is effected by, first, reducing the oxo function of the lactone ring to hydroxyl, followed by olefination to form a vinyl ether, then oxidation of the double bond to insert hydroxy groups and form a compound of formula (VI):

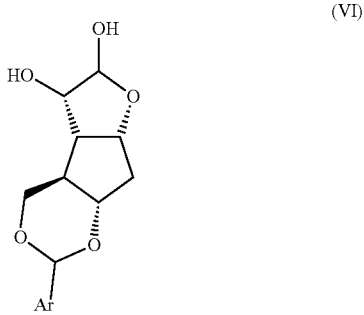

(VI)

and then oxidation thereof to form the aldehyde compound of formula (V).

4. The process of claim 3 wherein reduction of the oxo function of the lactone ring of compound (IV) is accomplished by reaction of compound (IV) with dibutylaluminum hydride (DIBAL) at temperatures below −20° C.

5. The process of claim 4 wherein the olefination to form a vinyl ether is accomplished by reaction with methane sulfonyl chloride and triethylamine in solution in a polar solvent at temperatures below −20° C.

6. The process of claim 5 wherein oxidation of the double bond is accomplished by reaction with 3-chlorobenzoic acid.

7. The process of claim 6 wherein oxidation to form the aldehyde compound is accomplished by reaction with sodium periodate.

8. The process of claim 1 wherein the nitrogen heterocycle is guanine protected at position 4, to produce entecavir as the antiviral carbanucleoside product.

9. The process of claim 8 wherein the protectant group at position 4 is OBn, Cl, or OSi($R_1R_2R_3$) where $R_1$, $R_2$, and $R_3$, are independently lower alkyl or phenyl.

* * * * *